US00PP35265P2

(12) United States Plant Patent
van Sambeek

(10) Patent No.: US PP35,265 P2
(45) Date of Patent: Jul. 11, 2023

(54) ***LAVANDULA* PLANT NAMED 'DOLAVIMPEAR'**

(50) Latin Name: *Lavandula dentata*
Varietal Denomination: Dolavimpear

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/991,535

(22) Filed: Nov. 21, 2022

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./263.1, 445
See application file for complete search history.

*Primary Examiner* — Karen M Redden
(74) *Attorney, Agent, or Firm* — C. Anne Whealy

(57) ABSTRACT

A new and distinct cultivar of *Lavandula* plant named 'Dolavimpear', characterized by its upright to somewhat outwardly spreading plant habit; medium plant height; freely branching growth habit; early and freely flowering habit; dark violet-colored flowers positioned on strong peduncles; and good garden performance.

2 Drawing Sheets

Figure 1:
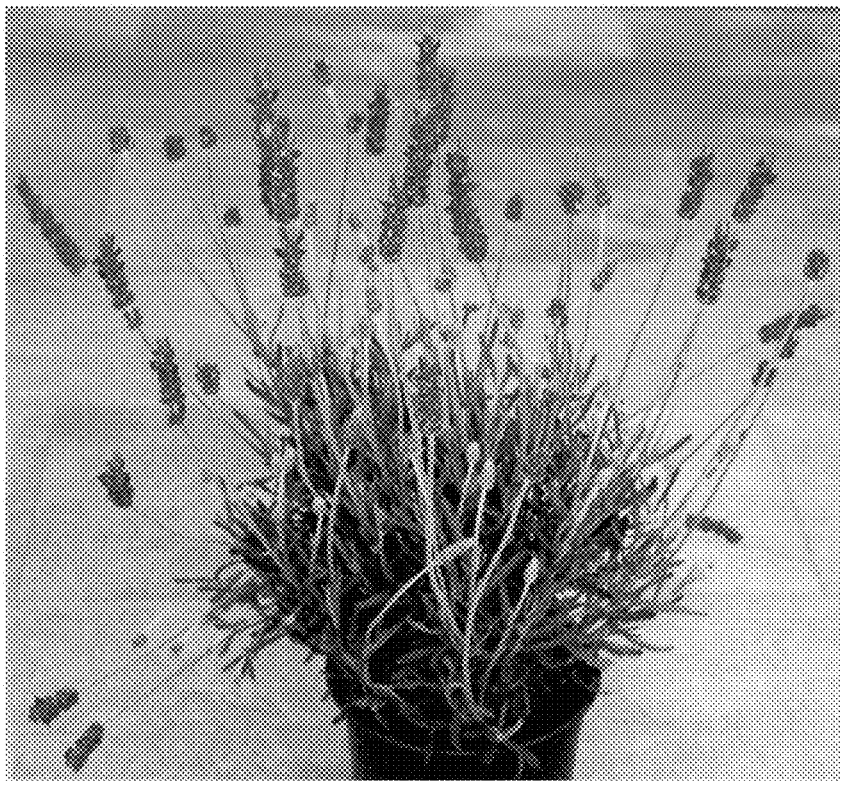

Botanical designation: *Lavandula dentata.*
Cultivar denomination: 'DOLAVIMPEAR'.

BACKGROUND OF THE INVENTION

The present invention relates to a new and distinct *Lavandula* plant, botanically known as *Lavandula dentata*, commonly referred to as Lavender and hereinafter referred to by the name 'Dolavimpear'.

The new *Lavandula* plant is a product of a planned breeding program conducted by the Inventor in Aalsmeer, The Netherlands. The objective of the breeding program was to develop new unique *Lavandula* plants with long flowering period and attractive plant form and flower coloration.

The new *Lavandula* plant originated from an open-pollination in April, 2017 of *Lavandula dentata* 'Dolavimp', disclosed in U.S. Plant Pat. No. 33,648, as the female, or seed, parent with an unknown selection of *Lavandula dentata* as the male, or pollen, parent. The new *Lavandula* plant was discovered and selected by the Inventor as a single flowering plant within the progeny of the stated open-pollination in a controlled environment in Aalsmeer, The Netherlands in June, 2018.

Asexual reproduction of the new *Lavandula* plant by terminal cuttings in a controlled greenhouse environment in Aalsmeer, The Netherlands since June, 2018 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new

*Lavandula* plant. These characteristics in combination distinguish 'Dolavimpear' as a new and distinct *Lavandula* plant:

1. Upright to somewhat outwardly spreading plant habit.
2. Medium plant height.
3. Freely branching growth habit.
4. Early and freely flowering habit.
5. Dark violet-colored flowers positioned on strong peduncles.
6. Good garden performance.

Plants of the new *Lavandula* differ primarily from plants of the female parent, 'Dolavimp' in the following characteristics:

1. Plants of the new *Lavandula* flower earlier than plants of 'Dolavimp'.
2. Plants of the new *Lavandula* are more freely flowering than plants of 'Dolavimp'.

Plants of the new *Lavandula* can be compared to plants of the *Lavandula dentata* 'Goodwin Creek Grey', not patented. In side-by-side comparisons, plants of the new *Lavandula* differ primarily from plants of 'Goodwin Creek Grey' in plant size as plants of the new *Lavandula* are shorter and more compact than plants of 'Goodwin Creek Grey'. In addition, leaves of plants of the new *Lavandula* are dark green in color whereas leaves of plants of 'Goodwin Creek Grey' are greyish green in color.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet (FIG. 1) is a side perspective view of a typical flowering plant of 'Dolavimpear' grown in a container.

Figure 2:
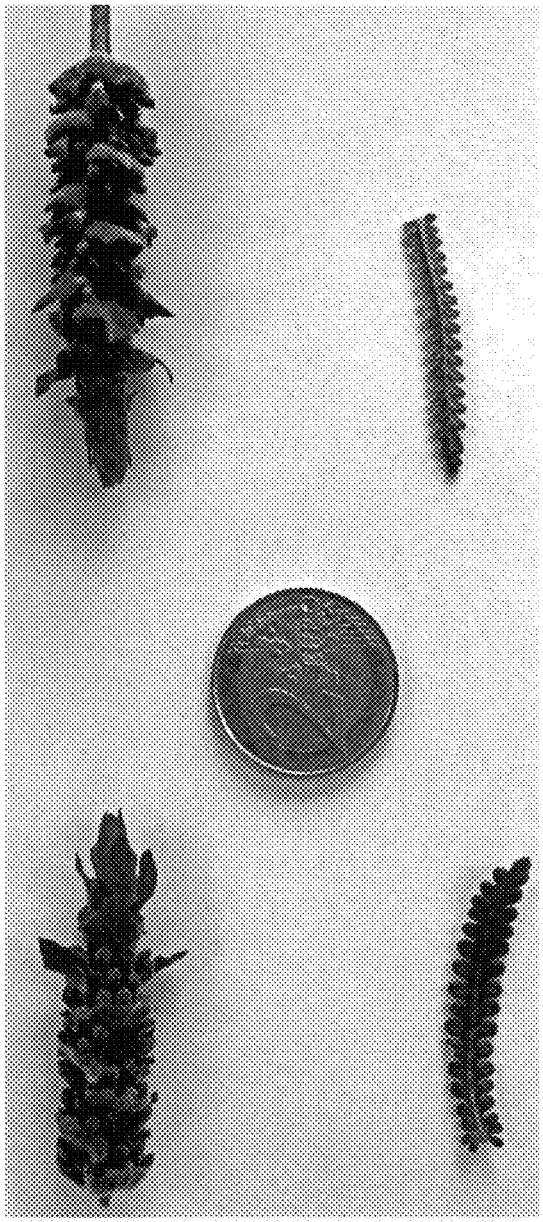

The photograph on the second sheet (FIG. 2) are close-up view of typical leaves and inflorescences of 'Dolavimpear'.

DETAILED BOTANICAL DESCRIPTION

The aforementioned photographs and following observations and measurements describe plants grown in 17-cm containers in Aalsmeer, The Netherlands during the summer initially in a greenhouse and finished in an outdoor nursery and under conditions and cultural practices which approximate those generally used in commercial *Lavandula* plant production. During the production of the plants, day temperatures averaged 21° C. and night temperatures averaged 15° C. Plants were 13 weeks old when the photographs and description were taken. In the following description, color references are made to The Royal Horticultural Society Colour Chart, Fifth Edition, except where general terms of ordinary dictionary significance are used.

Botanical classification: *Lavandula dentata* 'Dolavimpear'.

Parentage:

*Female, or seed, parent.*—*Lavandula dentata* 'Dolavimp', disclosed in U.S. Plant Pat. No. 33,648.

*Male, or pollen, parent.*—Unknown selection of *Lavandula dentata*, not patented.

Propagation:

*Type.*—Terminal vegetative cuttings.

*Time to initiate roots, summer.*—About 16 days at temperatures about 26° C.

*Time to initiate roots, winter.*—About three weeks at temperatures about 23° C.

*Time to produce a rooted young plant, summer.*—About 24 days at temperatures about 23° C.

*Time to produce a rooted young plant, winter.*—About four weeks at temperatures about 18° C.

*Root description.*—Medium in thickness, fibrous; typically white to light yellow in color, actual color of the roots is dependent on substrate composition, water quality, fertilizer type and formulation.

*Rooting habit.*—Moderately freely branching; medium density.

Plant description:

*Plant and growth habit.*—Herbaceous perennial; upright to somewhat outwardly spreading plant habit; medium plant height; broadly obovate in overall plant shape; freely branching habit; moderately vigorous growth habit; rapid growth rate; flowers arranged in verticillasters on crowded spikes with showy terminal flower bracts.

*Plant height, soil level to top of foliar plane.*—About 24 cm.

*Plant height, soil level to top of floral plane.*—About 41 cm.

*Plant width.*—About 51 cm.

*Lateral branch description.*—Quantity per plant: Freely branching with about three primary lateral branches each with about 16 secondary lateral branches developing per plant. Length: About 33 cm. Diameter: About 6 mm. Internode length: About 1.3 cm. Strength: Strong. Aspect: Erect to about 40° from vertical. Texture and luster: Pubescent; glossy. Color, when developing and developed: Close to 143C; if woody, close to 165A.

*Leaf description.*—Arrangement: Opposite and decussate, simple; sessile. Length: About 5 cm. Width: About 8 mm. Shape: Linear. Apex: Acute. Base: Truncate. Margin: Crenate with deep parallel lobes. Texture and luster, upper surface: Smooth, glabrous; glossy. Texture and luster, lower surface: Pubescent; semi-glossy. Fragrance: Strongly aromatic, pungent. Venation pattern: Pinnate. Color: Developing leaves, upper surface: Close to 146A. Developing leaves, lower surface: Close to 146B. Fully expanded leaves, upper surface: Close to 147A; venation, close to 146A. Fully expanded leaves, lower surface: Close to 146A; venation, close to 146A.

Flower description:

*Flower type, arrangement and habit.*—Single bilabiate flowers arranged in compact verticillasters on crowded terminal spikes; freely flowering, about 78 flowers developing per inflorescence and about 5,472 flowers developing per plant during the flowering season; flowers with two-lobed upper lip and three-lobed lower lip; flowers face mostly upright to outwardly on the spike; inflorescences with showy terminal flower bracts; flowers sessile.

*Natural flowering season.*—Flowering is continuous from June to August in The Netherlands; early flowering habit, plants begin flowering about seven weeks after planting.

*Flower longevity on the plant.*—Inflorescences last about three to four weeks on the plant; flowers persistent.

*Fragrance.*—Strongly fragrant; typical lavender scent.

*Flower buds.*—Length: About 6 mm. Diameter: About 2 mm. Shape: Elliptic. Texture and luster: Pubescent; glossy. Color: Close to 143A variably tinged with close to 187A.

*Inflorescence size.*—Height: About 6 cm. Diameter: About 1.5 cm.

*Flower size.*—Diameter: About 3 mm by 4 mm. Depth (height): About 7 mm. Throat diameter: About 1 mm. Tube length: About 5 mm. Tube diameter: About 1 mm.

*Petals.*—Quantity and arrangement: Upper lip, two-lobed and lower lip, three-lobed. Length: About 1 mm. Width: About 1 mm. Shape: Linear; proximally, fused into a tube. Apex: Obtuse, rounded. Margin: Entire; not undulate. Texture and luster, upper and lower surfaces: Smooth, glabrous; matte. Texture, throat and tube: Smooth, glabrous; matte. Color: When opening, upper and lower surfaces: Close to N88A. Fully opened, upper and lower surfaces: Close to N88B; venation, close to N88B; color does not change with subsequent development. Throat: Close to N88B; venation, close to N88B. Tube: Close to NN155D; venation, close to NN155D.

*Terminal flower bracts.*—Quantity and arrangement: About four positioned at inflorescence apex. Length: About 1.2 cm. Width: About 1 cm. Shape: Rhomboidal. Apex: Acute. Margin: Entire. Color, upper and lower surfaces: Close to 79A.

*Basal flower bracts.*—Quantity and arrangement: Subtending the flowers is a single basal flower bract. Length: About 1.2 cm. Width: About 1 cm. Shape: Rhomboidal. Apex: Acute. Margin: Entire. Texture, upper surface: Pubescent. Texture, lower surface: Smooth, glabrous. Color, upper surface: Close to 137C. Color, lower surface: Close to 137C variably overlain with close to N187A.

*Calyx.*—Arrangement: Five sepals fused forming an urceolate calyx. Length: About 7 mm. Diameter: About 2 mm. Sepal texture and luster, upper surface: Pubescent; glossy. Sepal texture and luster, lower surface: Smooth, glabrous; glossy. Sepal color: When opening and fully opened, upper surface: Distally, close to 187A and proximally, close to 147B. When opening and fully opened, lower surface: Close to 146B.

*Peduncles.*—Length: About 22 cm. Diameter: About 2 mm. Aspect: Upright. Strength: Strong. Texture and luster: Pubescent; semi-glossy. Color: Close to 143A variably tinged with close to NN187A.

*Reproductive organs.*—Stamens: Quantity per flower: Four. Filament length: About 1 mm. Filament color: Close to NN155D. Anther shape: Rounded; basifixed. Anther size: About 1 mm by 1 mm. Anther color: Close to 200A. Pollen amount: Abundant. Pollen color: Close to 15A. Pistils: Quantity per flower: One. Pistil length: About 5 mm. Stigma shape: Capitate. Stigma diameter: About 0.2 mm. Stigma color: Close to 203A. Style length: About 3 mm. Style color: Close to NN155D. Ovary color: Close to 144B.

*Seeds and fruits.*—To date, seed and fruit production has not been observed on plants of the new *Lavandula.*

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain, wind and to tolerate temperatures ranging from −15° C. to about 35° C. and to be suitable for USDA Hardiness Zone 7.

It is claimed:

1. A new and distinct *Lavandula* plant named 'Dolavimpear' as illustrated and described.

* * * * *